United States Patent [19]

Berscheid et al.

[11] Patent Number: 5,037,971
[45] Date of Patent: Aug. 6, 1991

[54] ANTHRACYCLINONE GLYCOSIDES CONTAINING AN N-OXIDIZED SUGAR

[75] Inventors: Hans G. Berscheid, Schwalbach am Taunus; Hans-Wolfram Fehlhaber, Idstein/Taunus; Hans P. Kraemer; Harald Zilg, both of Marburg, all of Fed. Rep. of Germany

[73] Assignee: Hoechst Aktiengesellschaft, Frankfurt am Main, Fed. Rep. of Germany

[21] Appl. No.: 463,791

[22] Filed: Jan. 8, 1990

Related U.S. Application Data

[63] Continuation of Ser. No. 170,392, Mar. 18, 1988, abandoned.

[30] Foreign Application Priority Data

Mar. 21, 1987 [DE] Fed. Rep. of Germany ....... 3709337

[51] Int. Cl.$^5$ ............................................. C07H 15/24
[52] U.S. Cl. ................................................... 536/6.4
[58] Field of Search ............................ 536/6.4; 514/34

[56] References Cited

U.S. PATENT DOCUMENTS 3,928,387  12/1975  Kierstead et al. ...................... 536/7.4
4,316,011  2/1982   Oki et al. ............................... 536/6.4
4,734,493  3/1988   Yoshimoto et al. ................... 536/6.4
4,737,583  4/1988   Huber et al. ........................... 536/6.4
4,795,808  1/1989   Berscherd et al. ..................... 536/6.4

OTHER PUBLICATIONS

"The Megalomicins. I. D-Rhodosamine, a New Dimethylamino Sugar," Journal of the Amer. Chem. Society, pp. 7505-7506, A. K. Mallams, vol. 91, No. 26 (1969).

Primary Examiner—Elli Peselev
Attorney, Agent, or Firm—Finnegan, Henderson, Farabow, Garrett, and Dunner

[57] ABSTRACT

The present invention relates to anthracycline derivatives of the formula I

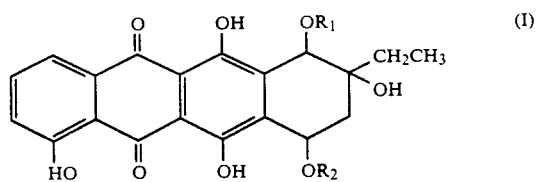

in which at least one of the two substitutents $R_1$ and $R_2$ represents an N-oxidized sugar or an N-oxidized sugar combination, and a chemical process for the preparation of these compounds and their use as medicaments for the treatment of malignant tumors.

4 Claims, No Drawings

ANTHRACYCLINONE GLYCOSIDES CONTAINING AN N-OXIDIZED SUGAR

This application is a continuation, of application Ser. No. 07/170,392 filed Mar. 18, 1988, now abandoned.

The present invention relates to anthracycline derivatives of the formula I

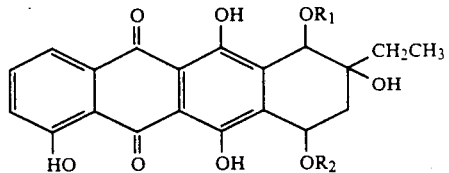

in which $R_1$ and $R_2$ are different and one of the two radicals represents the sugar unit L-rhodosamine (Roa) of the formula

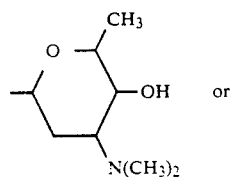

its N-oxide of the formula

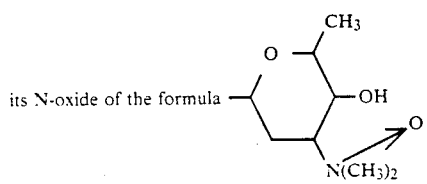

whilst the other represents the sugar combination L-rhodosamine-L-rhodinose-L-rhodinose (Roa-Rod-Rod) of the formula

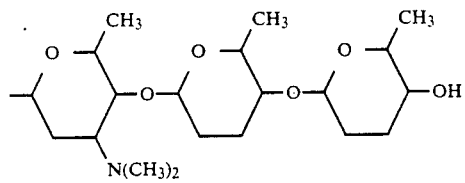

or L-rhodosamine-L-rhodinose-L-aculose (Roa-Rod-Acu) of the formula

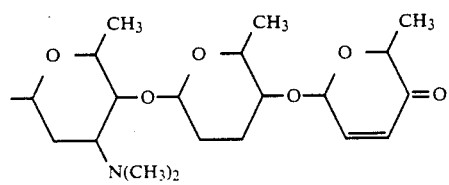

or L-rhodosamine-2-deoxy-L-fucose-L-cinerulose A (Roa-dF-Cin-A) of the formula

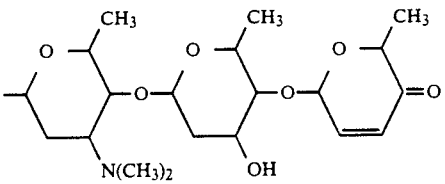

or L-rhodosamine-2-deoxy-L-fucose-L-cinerulose B (Roa-dF=Cin B) of the formula

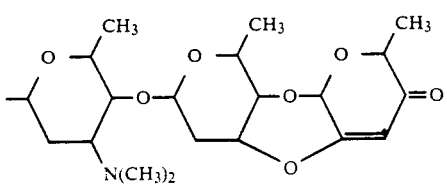

or L-rhodosamine-L-rhodinose-L-cinerulose A (Roa-Rod-Cin A) of the formula

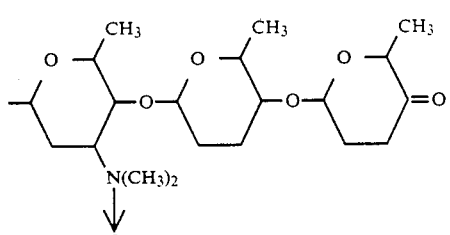

or L-rhodosamine-N-oxide-L-rhodinose-L-rhodinose (Roa-N-oxide-Rod-Rod) of the formula

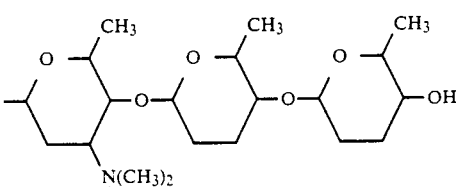

or L-rhodosamine-N-oxide-L-rhodinose-L-aculose (Roa-N-oxide-Rod-Acu) of the formula

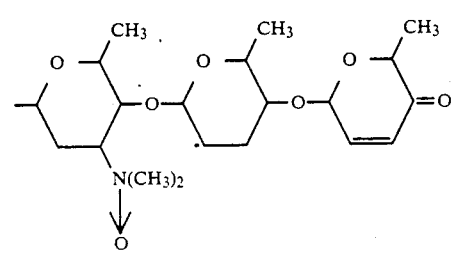

or L-rhodosamine-N-oxide-L-rhodinose-L-cinerulose A (Roa-N-oxide-Rod-Cin A) of the formula or L-rhodosamine-N-oxide-2-deoxy-L-fucose-L-cinerulose A (Roa-N-oxide-dF-Cin A) of the formula or L-rhodosamine-N-oxide-2-deoxy-L-fucose-L-cinerulose B (Roa-N-oxide-dF-Cin B) of the formula or L-rhodosamine-N-oxide-L-rhodinose-L-cinerulose A (Roa-N-oxide-Rod-Cin A) of the formula with the proviso that at least one of the two radicals $R_1$ and $R_2$ represents the corresponding sugar N-oxide.

The present invention furthermore relates to a process for the preparation of the compounds of the formula I, which comprises converting one of the compounds described in EP-A-0,131,942 and EP-A2-0,207,463, of the formula II in which one of the two substituents $R_3$ and $R_4$ represents one of the sugar combinations Roa-Rod-Rod, Roa-Rod-Acu, Roa-dF-CinA, Roa-Rod-CinA, Roa-dF-Rod or Roa-dF=CinB, the other represents the sugar unit Roa, CinB denoting cinerulose B and dF=CinB denoting that the two sugar units are linked by an additional ether bridge as well as by the customary glycosidic bond, into the amine oxide by treatment with an oxygen transfer reagent.

The N-oxidation reaction is carried out at temperatures between 0° and 35° C., preferably at 10°–30° C. The reaction time can be several hours to days, but varies for each of the compounds.

When the reaction has been carried out, the desired compounds are enriched out of the reaction medium by partition between aqueous buffer solutions and organic solvents and are isolated and purified by column chromatography or preparative layer chromatography, preferably on silica gel or reverse phases.

The following reagents are possible for this reaction: $H_2O_2$, peracids, such as, for example, m-chloroperbenzoic acid, peracetic acid, monopermaleic acid and trifluoroperacetic acid; and hydroperoxides, such as, for example, 2-hydroperoxyhexafluoro-2-propanol (Ganem et al., Tetrahedron Letters 21, 689 (1980)) or 3-bromo-4,5-dihydro-5-hydroperoxy-4,4-dimethyl-3,5-diphenyl-2H-pyrazole (Baumstark et al., Tetrahedron Letters 22 4591 (1981)).

The reaction can also be carried out microbially with suitable microorganisms or enzymes isolated therefrom, for example with Streptomyces purpurascens (DSM 2658).

The reaction is preferably carried out with $H_2O_2$ in a suitable solvent, for example in a lower alkanol or ketone, in water or aqueous buffer solutions at a temperature between 10° and 70° C. and a pH between 3 and 8.

The process according to the invention gives, for example, the following compounds, which are red, generally amorphous substances which are readily soluble in methanol, ethyl acetate, chloroform and toluene but insoluble in water and hexane and can be characterized by thin-layer chromatography on silica gel 60 $F_{254}$ (Merck), preferably with the mobile phase system chloroform/methanol/glacial acetic acid/water/triethylamine=80/10/10/2/0.01.

The detection of the formation of the compounds, quantitative monitoring of the reaction and purity testing can advantageously also be carried out by analytical high performance liquid chromatography:

Column: lichrospher ®100 RP-18.5 μm, 4×250 mm (Merck)
Mobile phase: 14% (volume) $CH_3CN$-86% (volume) buffer solution
Buffer solution: 20% (volume) triethylamine in water, brought to pH 3 with orthophosphoric acid (85% strength)
Flow rate: 0.5 ml/min
Detection: 254 nm or 495 nm
Retention time:
  Cytorhodine S about 55 minutes
  Cytorhodine S N-oxide about 80 minutes
  Cytorhodine S bis-N-oxide about 140 minutes The compounds according to the invention have a cytostatic activity, that is to say a therapeutic action against tumors, in particular malignant tumors in animals and humans.

The compounds and their acid addition salts can therefore be used as medicaments for the treatment of tumors. The compounds can be administered in various ways, depending on the dosage form.

The compounds or their acid addition salts, for example with D-gluconic acid, are usually administered as a mixture with pharmaceutically suitable excipients or diluents. They can thus be administered, for example, individually or as a mixture together with excipients, such as maltose or lactose, or as non-toxic complexes, for example as a deoxyribonucleic acid complex.

A typical mode of administration is injection of a solution of the compound according to the invention in distilled water or in physiological saline solution. The solutions can be injected intraperitoneally, intravenously or intraarterially.

The daily dose and unit dose can be specified from animal experiments and also from in vitro tests such that the total dose administered continuously or in intervals does not exceed a previously determined range. The total dose for a treatment cycle is thus about 0.5–5 mg/kg of body weight. This dose can be administered in appropriate fractions over a period of 7 days. However, it is clear that concrete doses for the treatment of humans or animals can be specified individually as a function of the particular situation of the patient, for example age, body weight, sex, sensitivity, diet, time of administration, other medicaments administered, physical condition of the patient and severity of the disease.

The preparation of the compounds according to the invention is described in the following example:

EXAMPLE a) About 400 mg of a compound of the abovementioned formula I, in which $R_1$ represents L-rhodosamine (Roa) and $R_2$ represents the sugar combination L-rhodosamine-2-deoxy-L-fucose-L-cinerulose B (Roa-df=C in B), with the designation "Cytorhodine S", were dissolved in 100 ml of methanol, the solution was stirred at room temperature, with exclusion of light, and 4 ml of hydrogen peroxide (30% strength) were added. The addition of $H_2O_2$ was repeated after 27 hours. The reaction was monitored by analytical high performance liquid chromatography.

After a total of 51 hours, excess reagent was destroyed by addition of palladium black and the reaction was thus ended.

The reaction solution was filtered with suction over a glass frit covered with a layer of Celite® and the filtrate was evaporated in vacuo on a rotary evaporator. The residue was taken up in 30 ml of aqueous Na acetate buffer, pH 3.5, 0.5 ml of 0.1M EDTA solution were added and the mixture was extracted 8 times with about 20 ml of $CHCl_3$ each time. The combined $CHCl_3$ extracts were washed with a little water and evaporated in vacuo. The residue weighed 244 mg.

After the pH had been brought to 7.0 with 1N NaOH, a further 44 mg of product were obtained by extracting twice with $CHCl_3$. According to analytical high performance liquid chromatography, the two extracts chiefly contain two newly formed compounds, in addition to a little unreacted Cytorhodine S educt.

| Reaction products: | | | |
|---|---|---|---|
| | % of N-oxide | Bis-N-oxide | Cytorhodine S |
| Main extract | 65 | 30 | 2 |
| Secondary extract | 25 | — | 10 |

The secondary extract also contains about 35% of a compound which has not yet been identified and has a retention time of about 110 minutes.

b) Isolation of the reaction products by "reversed phase" high performance liquid chromatography:

About 240 mg of the main extract were dissolved in 20 ml of the mobile phase $CHCl_3$/MeOH/10% ammonium acetate in $H_2O$ 150:1050:375 and the solution was chromatographed in a 3.2×25 cm steel column on 110 g of Lichrospher® 100 RP-18, 10μ (Merck) at a flow rate of 2 ml/minute. The progress of the elution was monitored with a flow photometer at a wavelength of 490 nm. The fractions of 5 ml were collected, after evaluation by thin-layer chromatography, and worked up. For this, they were diluted with half the volume of water, $CHCl_3$ was added until the phases separated and the $CHCl_3$ phase was separated off, washed with $H_2O$, dried over $Na_2SO_4$ and evaporated in vacuo. The following were obtained:

| Fraction | mg | Compound |
|---|---|---|
| 38–47 | 40 | Cytorhodine S bis-N-oxide |
| 100–150 | 90 | Cytorhodine S N-oxide |

Cytorhodine S N-oxide (formula I where $R_1$=Roa N-oxide and $R_2$=Roa-df=CinB): 1H-NMR in FIG. 1.

Absorption spectrum: 235 (4.6); 254 (4.3); 293 (3.86); 496 (4.17).

$C_{48}H_{64}N_2O_{18}$, calculated MW 956 (confirmed by FAB-MS).

Cytorhodine S bis-N-oxide (formula I where $R_1$=Roa N-oxide and $R_2$=Roa N-oxide-df=CinB): 1H-NMR in FIG. 2

Absorption spectrum: 235 (4.6); 252 (4.3); 294 (3.87), 495 (4.18).

$C_{48}H_{64}N_2O_{19}$, calculated MW 972 (confirmed by RBA-MS).

The compounds in the above example were identified under the measurement conditions described below:

The proton resonance spectra (1H-NMR spectra) were measured on a HX-270 BRUKER Fourier-Transform nuclear magnetic resonance spectrometer at 270 MHZ. The concentrations were 2–4 mg/0.5 ml of 99.8% pure $CDCl_3$; immediately after the preparation, the solutions were shaken with 0.1 ml of 5% strength $Na_2CO_3$ in 99.5% pure $D_2O$.

The signals marked with an asterisk in the figures originate from low molecular weight impurities in the o/oo region and solvent residues.

The mass spectra were measured on an MS-902 S, AEI mass spectrometer using a FAB (Fast Atom Bombardment) ion source. The substances were introduced into the ion source in a matrix of 3-nitrobenzyl alcohol or thioglycerol, partly with the addition of ammonium chloride.

The absorption spectra were measured in the range from 200–700 nm in 10% 1N HCl in methanol.

The substance concentration was 10–30 mg/l; the absorption maxima in nm and the molar extinction coefficients (log ε) are given.

We claim:

1. A compound of the formula I

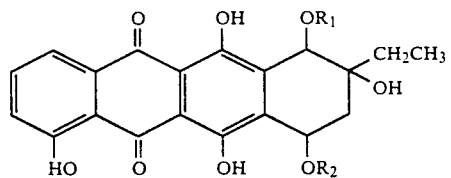

in which $R_1$ and $R_2$ are different and one of the two radicals represents the sugar unit L-rhodosamine (Roa) of the formula

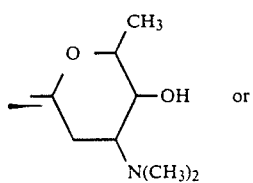

its N-oxide of the formula whilst the other represents the sugar combination L-rhodosamine-L-rhodinose-L-rhodinose (Roa-Rod-Rod) of the formula

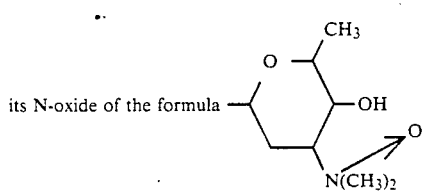

or L-rhodosamine-L-rhodinose-L-aculose (Roa-Rod-Acu) of the formula

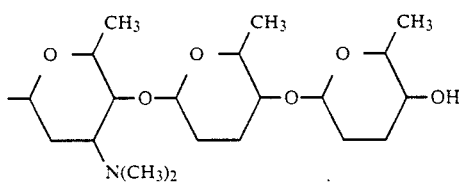

or L-rhodosamine-2-deoxy-L-fucose-L-cinerulose A (Roa-df-Cin-A) of the formula

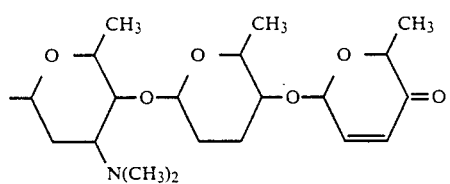

or L-rhodosamine-2-deoxy-L-fucose-L-cinerulose B (Roa-df=Cin B) of the formula

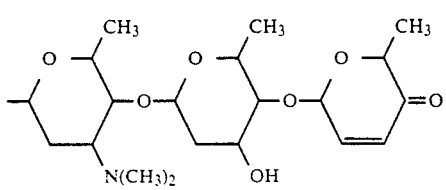

or L-rhodosamine-L-rhodinose-L-cinerulose A (Roa-Rod-Cin A) of the formula

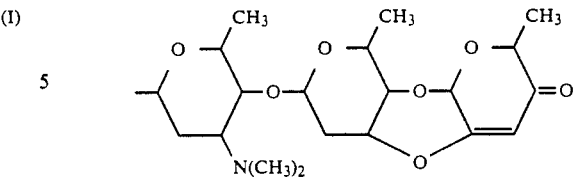

or L-rhodosamine-N-oxide-L-rhodinose-L-rhodinose (Roa-N-oxide-Rod-Rod) of the formula

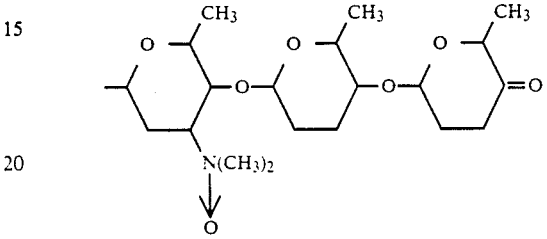

or L-rhodosamine-N-oxide-L-rhodinose-L-aculose (Roa-N-oxide-Rod-Acu) of the formula

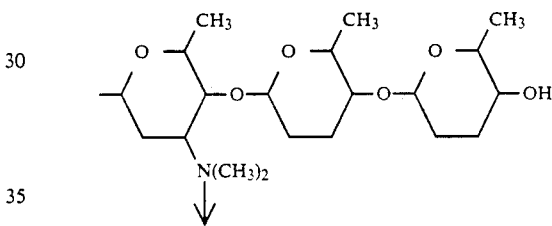

or L-rhodosamine-N-oxide-L-rhodinose-L-cinerulose A (Roa-N-oxide-Rod-Cin A) of the formula

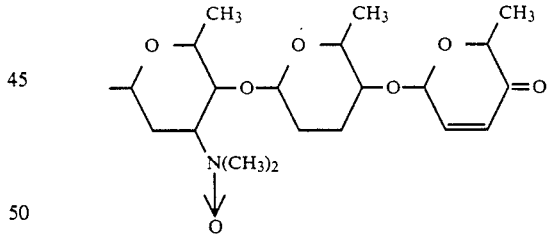

or L-rhodosamine-N-oxide-2-deoxy-L-fucose-L-cinerulose A (Roa-N-oxide-dF-Cin A) of the formula

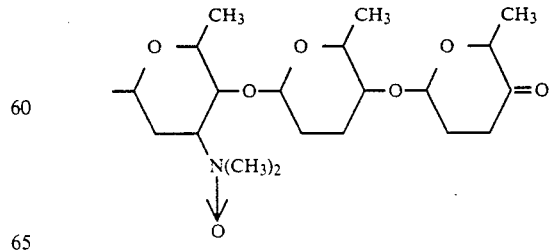

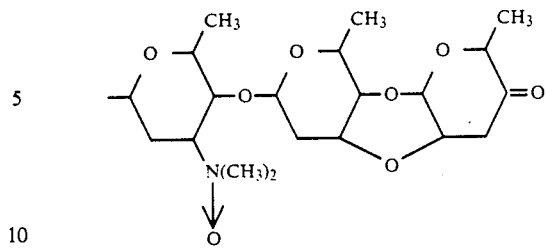

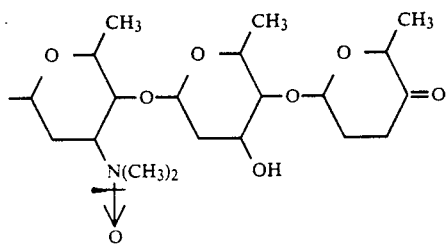

or L-rhodosamine-N-oxide-2-deoxy-L-fucose-L-cinerulose B (Roa-N-oxide-dF-C in B) of the formula or L-rhodosamine-N-oxide-L-rhodinose-L-cinerulose A (Roa-N-oxide-Rod-Cin A) of the formula

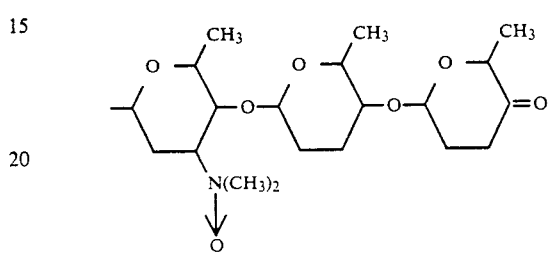

with the proviso that at least one of the two radicals $R_1$ and $R_2$ represents the corresponding sugar N-oxide.

2. A compound as claimed in claim 1, wherein $R_1$ represents L-rhodosamine N-oxide.

3. A compound as claimed in claim 2, wherein $R_2$ represents the sugar combination Roa-dF=CinB.

4. A compound as claimed in claim 2, wherein $R_2$ represents the N-oxidized sugar combination Roa N-oxide-dF=CinB.

* * * * *

UNITED STATES PATENT AND TRADEMARK OFFICE
CERTIFICATE OF CORRECTION

PATENT NO. : 5,037,971

DATED : August 06, 1991

INVENTOR(S) : Hans G. Berscheid et al.

It is certified that error appears in the above-identified patent and that said Letters Patent is hereby corrected as shown below:

Title page, item (54), and column 1, line 2, delete "N-".

Abstract, line 3, change "substitutents" to --substituents--.

Abstract, Figure I, first ring, change  to .

Claim 1, column 7, line 5, change  to .

Claim 1, column 7, line 56, change "df" to --"dF"--.

Claim 1, column 7, line 68, change "df" to --dF"--.

UNITED STATES PATENT AND TRADEMARK OFFICE
CERTIFICATE OF CORRECTION

PATENT NO. : 5,037,971

DATED : August 06, 1991

INVENTOR(S) : Hans G. Berscheid et al.

It is certified that error appears in the above-identified patent and that said Letters Patent is hereby corrected as shown below:

Claim 1, column 9, line 34, change "C in " to --Cin--.

Signed and Sealed this

Thirteenth Day of April, 1993

Attest:

STEPHEN G. KUNIN

*Attesting Officer*   Acting Commissioner of Patents and Trademarks